United States Patent [19]

Reineke

[11] Patent Number: 4,820,853
[45] Date of Patent: Apr. 11, 1989

[54] PROCESS FOR THE PREPARATION OF ALKYL DIARYL PHOSPHITES AND DIARYL HALOPHOSPHATES

[75] Inventor: Karl E. Reineke, Brewster, N.Y.

[73] Assignee: Akzo America Inc., New York, N.Y.

[21] Appl. No.: 28,440

[22] Filed: Mar. 20, 1987

[51] Int. Cl.$^4$ .......................... C07F 9/141; C07F 9/14
[52] U.S. Cl. ......................................... 558/99; 558/115
[58] Field of Search .................. 558/99, 115, 202, 218

[56] References Cited

U.S. PATENT DOCUMENTS

| | | | |
|---|---|---|---|
| 2,678,330 | 5/1954 | Van Gorder et al. | 558/202 |
| 3,987,129 | 10/1976 | Pivawer et al. | 558/122 |
| 4,237,075 | 12/1980 | Gough | 558/95 |

OTHER PUBLICATIONS

Kosolapoff et al., "Organic Phosphorus Compounds", vol. 5, p. 33; vol. 6, p. 249 (1974).

Primary Examiner—Anton H. Sutto
Attorney, Agent, or Firm—Richard P. Fennelly; Louis A. Morris

[57] ABSTRACT

Substantially pure alkyl diaryl phosphites can be prepared by reacting a purified alkyl dihalophosphite with a phenol. Diaryl halophosphates of increased purity can be prepared by halogenating the purified alkyl dihalophosphites. This method avoids the by-products and unreacted starting materials generally included as impurities in prior art processes.

17 Claims, No Drawings

PROCESS FOR THE PREPARATION OF ALKYL DIARYL PHOSPHITES AND DIARYL HALOPHOSPHATES

The present invention relates to a new process for preparing alkyl diaryl phosphites and diaryl halophosphates in high yields with limited by-product formation and loss of reactants.

BACKGROUND OF THE INVENTION

Diaryl chlorophosphate finds extensive uses in the preparation of antibiotic products such as imipenem and in peptide synthesis, Fieser and Fieser, *Reagents For Organic Synthesis,* Wiley, 1967, p. 346.

Past methods of preparation of diaryl chlorophosphates have included reacting $POCl_3$ with a stoichiometric amount of phenol. Even using a 1:1 mole ratio of $POCl_3$ to phenol, three products are formed, i.e., phenyl dichlorophosphate, diphenyl monochlorophosphate and triphenyl phosphate, as well as unreacted $POCl_3$, the first being in the predominant amount. While the $POCl_3$ can be distilled off and recycled, the phenyl dichlorophosphate is difficulty separable and even when separated finds little utility in making the desired product. The triphenyl phosphate can be separated by distillation but is not usable in formation of the product. Phosphate as well as phenol values are, therefore, lost.

In U.S. Pat. No. 3,965,220, it has been proposed to prepare diaryl phosphorochloridates by first reacting phosphoryl chloride with a molar equivalent of phenol in the presence of an amine at a temperature ranging from about 85° C. to about 135° C. to prepare the aryl phosphorodichloride followed by reacting that product with a molar equivalent of the same or different phenol at higher temperatures. While high yields of phosphorochloridate are claimed using this process, the reaction will still form triaryl phosphate, and other non-useful by-products.

In the preparation of alkyl iodides the following reaction scheme has been set forth:

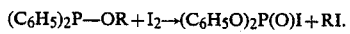

$(C_6H_5)_2P-OR + I_2 \rightarrow (C_6H_5O)_2P(O)I + RI.$

This is known in a paper entitled "The Reactions of Phenyl Esters of Phosphorus Acid with Iodine", JACS, 75 (1953) pp. 3145–3148. The starting reactant is prepared by reacting diphenyl chlorophosphite with cyclohexanol in the presence of pyridine and an ether solvent. By this means a cyclohexyl diphenyl phosphite is prepared. This product, when reacted with iodine, will give the alkyl iodide. This reaction has the same inherent problem as the previously discussed reaction. The diaryl chlorophosphite is prepared by reacting $PCl_3$ with two moles of phenol. A mixture of mono-, di- and triphenyl phosphites is prepared which requires separation in order to obtain a pure starting material. As the molecular weights rise because of the weight of the aryl substituents, the difficulty in separating the products by distillation increases. This is particularly true when the aryl group is substituted such as in the case of a dihalo substituent.

Part of this problem is avoided in another method for converting alcohols into iodides by replacing the diphenyl chlorophosphite with o-phenylene chlorophosphite prepared from catechol. In this case the o-phenylene chlorophosphite is a stable reagent, prepared in a form which can be easily separated by distillation (see the paper entitled "A Useful Method for the Conversion of Alcohol Into Iodides", E. J. Corey et al., J. Org. Chem., 32 (1967) pp. 4160–4161).

It has now been found that alkyl diaryl phosphites and diaryl halophosphates can be easily prepared under conditions that reduce by-product formation and allow product recovery in high yields.

SUMMARY OF THE INVENTION

In accordance with the present invention there is provided a process for preparing alkyl diaryl phosphites of high purity which comprises reacting a substantially pure alkyl dihalophosphite with a phenol in the presence of an acid acceptor and a solvent, the acid acceptor being a base which will not react with the alkyl dihalophosphite, separating the reaction product of the acid acceptor and the halo acid by-product such as by filtration, and removing excess amine and phenol to obtain the desired alkyl diaryl phosphite. By this process, a wide range of alkyl diaryl phosphites can be prepared in high purity. Some of these alkyl diaryl phosphites can be converted into diaryl halophosphates by halogenating the alkyl diaryl phosphite with free halogen. Other uses for the alkyl diaryl phosphites depends on the substituent groups.

The alkyl dihalophosphite can be easily prepared and separated into a substantially pure material by distillation because of its low molecular weight. The reaction of that product with phenol cannot form triaryl phosphite which is formed only when $PCl_3$ is present. Since the $PCl_3$ can be easily separated by distillation, the alkyl dihalophosphite will react with two moles of phenol to provide substantially pure alkyl diaryl phosphite and subsequently substantially pure diaryl halophosphate.

DETAILED DESCRIPTION OF THE INVENTION

As used herein, the definitions of "alkyl", "aryl" and "halogen" depend on the reaction being discussed. In preparing the alkyl dihalophosphite, the halogen can be chlorine or bromine. In the halogenation of the alkyl diaryl phosphite, chlorine or bromine or iodine can be used. Certain alkyl and aryl groups are satisfactory for preparing the alkyl diaryl phosphite. However, some of these groups are incompatible with a halogenation reaction. In defining the alkyl dihalophosphite and the alkyl diaryl phosphite when there is no subsequent halogenation reaction, the formulae $A-O-PX_2$ and $A-O-P(OAr)_2$ will be used. In defining the alkyl diaryl phosphite and the diaryl halophosphate prepared therefrom by halogenation, the formulae $A^1-O-P(OAr^1)_2$ (as reactant) and $(Ar^1O)_2P(O)Y$ will be used. These groups will be fully defined hereinafater.

The alkyl dihalophosphite ($A-O-PX_2$) can be prepared by numerous known techniques. In one, an excess of $PX_3$, wherein X is chlorine or bromine, can be reacted with an alcohol (A—OH) under anhydrous condition with cooling, i.e., less than 10° C. preferred. While the reaction can be conducted in an inert solvent, solvent removal at the end of the reaction makes this procedure less desirable.

As used herein, "A" represents alkyl, alkenyl, alkynyl, cycloalkyl, cycloalkenyl, cycloalkynyl, heterocyclyl, aralkyl and substituted derivates thereof such as with halogen. Thus, alkyl represents alkyl, e.g., methyl, ethyl, propyl, butyl, amyl, hexyl, heptyl, octyl, decyl, undecyl, dodecyl, pentadecyl, hexadecyl, octadecyl, nonadecyl and eicosyl, whether straight or branched chain configuration; cycloalkyl, e.g., cyclopropyl, cyclobutyl, cyclopentyl, ethylcyclopropyl, cyclohexyl, methylcyclopentyl, methylcyclohexyl, decahydronaphthyl, bicyclohexyl (cyclohexylcyclohexyl), tetradecahydrophenanthryl, tricyclohexylmethyl; alkenyl, e.g., ethenyl, propenyl, butenyl, isobutenyl, pentenyl, methylbutenyl, trimethylethenyl, hexenyl, heptenyl, octenyl, nonenyl, decenyl, dodecenyl, tridecenyl, hexadecenyl, octadecenyl, eicosenyl; cycloalkenyl, e.g., cyclopropenyl, cyclopentenyl, cyclohexenyl, cyclohexylcyclohexenyl; alkynyl, e.g., ethynyl, propynyl, butynyl, pentynyl, hexynyl, heptynyl, octynyl, nonynyl, decynyl, tridecynyl, octadecynyl, eicosynyl; cycloalkynyl, e.g., 1-cycloden-4-yl; heterocyclic radicals containing oxygen or sulfur in the heterocyclic ring, e.g., thiophenyl, furanyl, tetrahydrofuranyl, pyranyl, sulfolanyl; aralkyl, e.g., benzyl and the like.

In a second technique, $PX_3$ in excess can be reacted under anhydrous conditions with an epoxide of the formula:

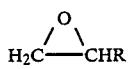

wherein R can be hydrogen (ethylene oxide) or "A" as defined above. The reaction is conducted with cooling, less than 10° C. being preferred, and can be conducted in an inert solvent though this is less preferred as the solvent must be removed upon completion of the reaction.

In another reaction sequence, trialkyl phosphite $(A-O)_3P$ and $PX_3$ can be reacted together until they equilibrate. Good yields are obtained but long reaction times are necessary.

Even though controlled conditions are used in these reactions, the product will contain trace amounts of dialkyl halophosphite, trialkyl phosphite and $PX_3$. It is essential that these trace products are separated from the alkyl dihalophosphite prior to further reaction as these impurities will carry through the main reaction. Since the impurities are based on low molecular weight alkyl groups, they are easily separable by ordinary means such as distillation. If the alkyl group is not intended to be part of the final product, the alkyl group can be selected solely on the basis of the ease of the separation of the alkyl dihalophosphite from the by-products. While the alkyl group can be methyl, the higher molecular weight alkyl groups provide products with greater differences in molecular weight as the number of halogens replaced increases. The difference in molecular weights is evidenced in greater differences in boiling points, thus allowing for easier fractional distillation. Preferably, "A" is an alkyl group of $C_1$ to $C_4$ carbons and the halosubstituted derivatives thereof. This separation can be by any means though fractional distillation is considered to be the most convenient method available.

If the alkyl group is removed during a later reaction step and not become part of the final product, the alkyl group must be removable by the reaction step, i.e., halogenation. The alkyl group cannot form unseparable byproducts or be hazardous to react. For this reason tertiary alcohols are less preferred. The definition of alkyl or "A" will be limited vis-a-vis those groups which can be removed by halogenation.

The alkyl dihalophosphite $(A-O-PX_2)$ is then reacted with a phenol (ArOH) to form the desired alkyl diaryl phosphite $(A-O-P-(OAr)_2)$ as can be seen by the following relationship;

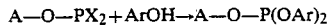

wherein "Ar" can be one or more and preferably 1–2 aryl rings including benzene and naphthalene, biphenyl and derivatives thereof substituted with halogen, alkoxy such as methoxy, alkyl such as $C_1$–$C_{20}$ or any other substituent which is unreactive with the alkyl dihalophosphite or halogen. Thus, "Ar" can be phenyl, alkylphenyl, halophenyl, arylphenyl, cycloalkylphenyl, napthyl, biphenyl, phenanthryl, anthracyl, terphenyl, quarterphenyl.

Included within "Ar" are specific phenols represented by phenol, o, m, p-cresol, o-ethylphenol, o, m, p-isopropylphenol, p-tert-butylphenol, p-tert-amylphenol, nonylphenol, xylenol, o, m, p-chlorophenol, p-bromophenol, p-iodophenol, dichlorophenol, trichlorophenol, pentachlorophenol, p-cumylphenol, o-cylohexylphenol, naphthol, methoxyphenol, ethoxyphenol, phenoxyphenol, nitrophenol, trifluoromethylphenol, allylphenol, benzylphenol, vanillin, 4-chloro-3,5-dimethylphenol, 4-chloro-1-naphthol, 2-chloro-4-nitrophenol, cyanophenol, di-tert-butylphenol, dimethoxyphenol, methylsalicylate, fluorophenol. Especially preferred of this group are phenol, cresol, cymylphenol, nonylphenol, chlorophenol, dichlorophenol, tert-butylphenol, xylenol, phenylphenol, isopropylphenol and mixtures thereof. In some uses, the aryl groups are used on the final compound as blocking groups which are later removed during the preparation of imipenem. The aryl groups can be selected on the basis of further reaction selectivity of the halophosphate. "Ar" is more preferably one aryl ring and most preferably one aryl ring substituted with one or two halogens.

The alkyl "A" and aryl ("Ar") groups may be unsubstituted, as described above, or substituted with any moiety which does not interfere with the reaction of preparing the alkyl diaryl phosphite.

The following radicals are illustrative of the substituents which may occur on the groups represented by alkyl ("A") and aryl ("Ar"): alkyl, cycloalkyl, alkenyl, cycloalkenyl, alkynyl, cycloalkynyl, and aryl as described above. Also, halo, e.g., chloro, bromo, fluoro, iodo; alkoxy, e.g., methoxy, propoxy, butoxy, hexoxy, decoxy; cycloalkoxy, e.g., cyclohexoxy, cyclobutoxy; alkenoxy, e.g., propenoxy; cycloalkenoxy, e.g., cyclopentenoxy; aryloxy, e.g., phenoxy, naphthoxy; cyano; nitro; isonitro; aldehyde; ketone, alkoxycarbonyl, e.g., methoxycarbonyl; aryloxycarbonyl, e.g., phenoxycarbonyl; alkylcarbonyloxy, e.g., acetyl; alkoxycarbonyloxy, e.g., acetoxy; arylcarbonyloxy, e.g., benzoyl; alkylthio, e.g., ethylthio; arylthio, e.g., phenylthio, naphthylthio, trihaloalkyl, e.g., trifluoromethyl; alkylsulfinyl, e.g., butylsulfinyl, arylsulfinyl, e.g., phenylsulfinyl; alkylsulfonyl, e.g., propylsulfonyl; arylsulfonyl, e.g., phenylsulfonyl.

The diaryl alkyl phosphites can be prepared by reacting the substantially pure alkyl dihalophosphite with the phenol in the presence of an acid acceptor, such as a tertiary amine including triethyl amine or pyridine, under sufficiently cooling to control the exotherm. The reaction is relatively quick but it may be desirable to continue reaction after addition of reactants for a period of time sufficient to provide the desired extent of reaction as can be readily determined by analysis. Since the reaction product between the acid acceptor and the halo-acid generated in the reaction can accelerate the hydrolysis of the alkyl diaryl phosphite, the acid acceptor reaction product must be separable without the need for water washing. Preferably, the reaction product of the acid acceptor and the halo-acid is a precipitate which can be separated from the solution of the reactor by filtration means. Acid acceptors can be illustrated by tertiary amines including triethyl amine as well as pyridine or any other acid acceptor which can be used in the reaction without interaction with the reaction other than the acid and which can form an acid acceptor reaction product which can be separated without water washing. The acid acceptor is used in an amount sufficient to accent the acid generated in the reaction.

After the reaction product of the acid acceptor and haloacid has been removed, the product can be washed to remove impurities. The product can be washed with a weak base solution (alkali metal hydroxide at up to 10% as illustrative) to remove unreacted phenol and other impurities. If desired, an optional water wash can precede the base wash (after removal of the acid acceptor - halo-acid product).

An acidic wash (HCl at up to 10% as illustrative) can be used to remove excess amine. A water wash can be used to remove any excess acid and a brine wash to remove any excess water.

The alkyl diaryl phosphites can be used as is or as intermediates in preparing other compositions. As part of this invention certain alkyl diaryl phosphites can be halogenated to form diaryl phosphorohalidates in high purity. The purity of the final product is dependent on the purity of the reactants. The invention is directed to the preparation of alkyl diaryl phosphite of an increased purity and this purity is reflected in the purity of the final product. Because of the propensity of halogen to react with a wide variety of substituents in a manner unsuited to preparing diaryl phosphorohalidates in high purity, the halogenated reaction will be represented as follows:

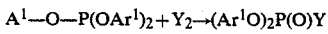

wherein Y is a halogen of chlorine, bromine or iodine; "$A^1$" represents alkyl, cycloalkyl, heterocyclyl, aralkyl and substituted derivatives thereof including methyl, ethyl, propyl, butyl, amyl, hexyl, heptyl, octyl, decyl, dodecyl, octadecyl, eicosyl, whether straight or branched chain; cycloalkyl, e.g., cyclopropyl, cyclobutyl, cyclopentyl, ethylcyclopropyl, cyclohexyl, methylcyclopentyl, methylcyclopentyl decahydronaphthyl, bicyclohexyl, tetradecahydrophenanthryl, tricyclohexylmethyl; heterocyclic radicals containing oxygen in the heterocyclic ring, e.g., tetrahydrofuranyl, and aralkyl such as benzyl. Groups such as alkenyl, cycloalkenyl, alkynyl, cycloalkynyl, alkenoxy and cycloalkenoxy, cyano, aldehyde, alkylthio, arylthio, alkylsulfinyl and arylsulfinyl should be avoided if the reaction products of the halogenation reaction are non-separable or the reaction is unsafe to run; and wherein "$Ar^1$" represents the aryl portion of the alkyl diaryl phosphite and the diaryl phosphorohalidate and can be 1-2 aryl rings including benzene and naphthalene, biphenyl and derivatives thereof substituted with halogen, alkoxy such as methoxy, alkyl such as $C_1$-$C_{20}$ or any other substituent which is unreactive with the alkyl dihalophosphite or halogen. Thus, aryl can be phenyl, alkylphenyl, halophenyl, arylphenyl, cycloalkylphenyl, napthyl, biphenyl, phenanthryl, anthracyl, terphenyl, quarterphenyl.

Included within "$Ar^1$" are specific phenols represented by phenol, o, m, p-cresol, o-ethylphenol, o, m, p-isopropylphenol, p-tert-butylphenol, p-tert-amylphenol, nonylphenol, xylenol, o, m, p-chlorophenol, p-bromophenol, p-iodophenol, dichlorophenol, trichlorophenol, pentachlorophenol, p-cumylphenol, o-cylohexylphenol, naphthol, methoxyphenol, ethoxyphenol, phenoxyphenol, nitrophenol, trifluoromethylphenol, allylphenol, benzylphenol, vanillin, 4-chloro-3,5-dimethylphenol, 4-chloro-1-naphthol, 2-chloro-4-nitrophenol, di-tert-butylphenol, dimethoxyphenol, methylsalicylate, fluorophenol. Especially preferred of this group are phenol, cresol, cymylphenol, nonylphenol, chlorophenol, dichlorophenol, tert-butylphenol, xylenol, phenylphenol, isopropylphenol and mixtures thereof. In some uses, the aryl groups are used on the final compound as blocking groups which are later removed during the preparation of imipenem. The aryl groups can be selected on the basis of further reaction selectivity of the chlorophosphate. "$Ar^1$" is preferably one aryl ring and more preferably one aryl ring substituted with halogen, such as in the 2,4 positions.

The alkyl ("$A^1$") and aryl ("$Ar^1$") groups may be unsubstituted, as described above, or radicals represented by alkyl ("$A^1$") and aryl ("$Ar^1$") may be substituted with any moiety which does not interfere with the halogenation reaction.

The following radicals are illustrative of the substituents which may occur on the groups represented by alkyl ("$A^1$") and aryl ("$Ar^1$"): alkyl, cycloalkyl and aryl as described above. Also, halo, e.g., chloro, bromo, fluoro, iodo; alkoxy, e.g., methoxy, propoxy, butoxy, hexoxy, decoxy; cycloalkoxy, e.g., cyclohexoxy, cyclobutoxy; aryloxy, e.g., phenoxy, naphthoxy; nitro; isonitro; ketone, alkoxycarbonyl, e.g., methoxycarbonyl; aryloxycarbonyl, e.g., phenoxycarbonyl; alkylcarbonyloxy, e.g., acetyl; alkoxycarbonyloxy, e.g., acetoxy; arylcarbonyloxy, e.g., benzoyl; trihaloalkyl, e.g., trifluoromethyl; alkylsulfonyl, e.g., propylsulfonyl; arylsulfonyl, e.g., phenylsulfonyl.

The halogenation reaction can be conducted using a solvent which is non-reactive with the halogen. The halogen is added at such a rate and under sufficient cooling and agitation to control the exotherm. A temperature of reaction between about 0° C. and about 10° C. is suggested. The product can be purified by removal of solvent and alkyl halide by distillation.

The product of this step of the invention is a diaryl halophosphate and can be prepared in extremely high purities depending upon the purity of the initial alkyl dihalophosphite. If the alkyl dihalophosphite is extremely pure, then the final product will be extremely pure. The process of the invention avoids the automatic formation of byproducts typical of reacting phosphorous trichloride or phosphorus oxychloride with an aryl compound.

In addition to utilizing the compounds of the invention in the preparation of antibiotics, the phosphites of the invention can be used as antioxidants, and the halophosphates can be used as intermediates in the preparation of flame retardants and lubricant additives.

The present invention will be more fully illustrated in the examples which follow:

EXAMPLE 1

Preparation of Ethyl bis(2,4-dichlorophenyl) phosphite 109.8 grams (0.674 mole) of 2,4-dichlorophenol was melted and charged into a three-neck reaction flask equipped with an addition funnel, a magnetic stirring bar, a thermometer and a nitrogen sparge. Also charged was 100 milliliters of toluene containing 250 parts per million water and 74.3 grams of triethyl amine which contained 650 parts per million water. The addition of these materials caused an exothermic reaction of dissolution and the temperature rose to 55° C.

49.4 grams (0.336 mole) of ethyl dichlorophosphite which has been previously distilled to a purity of 96% was charged to the reaction flask through the addition funnel over a period of 1¼ hours with ice water cooling. The temperature during addition varied between about 24° C. to about 70° C. 200 milliliters of additional toluene was added to aid stirring of the thick slurry towards the end of the addition period. The slurry was allowed to stir over the weekend.

The following Monday, the product was filtered and rinsed twice with 100 milliliters of toluene for each rinse, the filtrate was transferred to a separatory funnel and washed twice with 100 milliliters 5% HCl; twice with 100 milliliters 5% sodium hydroxide solution; once with 100 milliliters water; and once with 100 milliliters brine. The organic layer was dried over magnesium sulfate, the magnesium sulfate was filtered off, and the filtrate was rotoevaporated under reduced pressure to remove volatiles. The product yield was 132.1 grams or 98% based on the weight of the initial reactants.

Gas chromatography area percent indicated the product contained 92.5% ethyl bis(2,4-dichlorophenyl) phosphite, 0.7% dichlorophenol, 3.2% ethyl bis(2,4-dichlorophenyl) phosphate and 2.3% tris(2,4-dichlorophenyl) phosphite.

EXAMPLE 2

Preparation of bis(2,4-dichlorophenyl) chlorophosphate

A 500 milliliter flask fitted with thermometer, magnetic stirring bar, and nitrogen sparge was charged through the sparge tube with 150 milliliters of CCl₄ and 129.8 grams (0.324 mole) of ethyl bis(2,4-dichlorophenyl) phosphite. The reaction mixture was sparged with nitrogen and cooled in an ice water bath. Chlorine was added initially at a rate of 0.1 gram/minute and later increased to 0.2 gram/minute under sparging, ice water cooling and agitation until a pale green color was noted in the reaction mixture. Addition required approximately 4 hours at temperatures below 10° C. Approximately 23 grams of chlorine was added.

The product was transferred to a tared 1 liter flask. All volatiles were evaporated off using a Rotovap rotary evaporator under reduced pressure. The product yield was 129.2 grams or 98.1% yield based on the weight of the initial starting materials.

Gas chromatographic analysis based on area percent on the evaporated product showed the following: 93.1% bis(2,4-dichlorophenyl) chlorophosphate; 4% tri(2,4-dichlorophenyl) phosphate; 0.4% 2,4-dichlorophenyl dichlorophosphate; 0.1% 2,4-dichlorophenol; and 2.3% unknowns (3).

Gas chromatographic analysis of the product against an internal standard showed 94.5% purity.

EXAMPLE 3

Preparation of bis(2,4-dichlorophenyl) chlorophosphate

A 1 liter 3 necked Morton flask fitted with a nitrogen sparge, an additional funnel, a mechanical stirrer and a thermocouple for monitoring reaction temperature was charged with 400 milliliters chlorobenzene. 140.6 grams (0.862 moles) of 2,4-dichlorophenol (containing about 1.4% 2,6-dichlorophenol) was melted and added. Triethylamine, 87.1 grams (0.862 mole), was added at once. The temperature rose to 54° C.

The reaction flask was cooled to 15° C. with an ice water bath and 78.2 grams of chloroethyl dichlorophosphite which had been previously distilled to a purity of about 97% was added by means of the addition funnel over a period of 10 minutes. An additional 50 milliliters chlorobenzene was added to aid stirring. During the addition of the dichlorophosphite, the temperature rose to 38° C. The funnel was rinsed with an additional 30 milliliters of chlorobenzene. A thick slurry was obtained.

The thick slurry was removed from the ice water bath and allowed to stir at ambient temperature for 21 hours. The slurry was then filtered. The triethylamine hydrochloride reaction product was rinsed with 150 milliliters chlorobenzene and then 100 milliliters chlorobenzene, the rinses being combined with the filtrate. Gas chromatography area percent at this point indicated 2% dichlorophenol, 0.4% bis(chloroethyl)-dichlorophenyl phosphate, 96.4% bis(dichlorophenyl)-chloroethyl phosphite, 0.2% tris(dichlorophenyl) phosphite and 0.1% tris(dichlorophenyl) phosphate.

The filtrate was washed once with 100 milliliters 5% HCl, once with 100 milliliters H₂O, once with 150 milliliters 5% NaOH, once with 100 milliliters 5% NaOH and once with 100 milliliters H₂O. Gas chromatography area percent indicated less than 0.5% dichlorophenol. The water was removed with anhydrous magnesium sulfate which was subsequently separated by filtration.

The volume of the chlorobenzene solution was reduced to about 600 milliliters on a rotary evaporator, and charged to a 1 liter flask fitted with a magnetic stirring bar, sparge tube for chlorine and nitrogen addition, outlet for nitrogen and a thermocouple. The flask was immersed in an ice water bath and the solution cooled to 3° C. Chlorine, diluted with nitrogen, was added at a rate of about 0.3 grams/minute until a pale green color was noted. Addition required about 2 hours and 28.85 grams chlorine was added. Temperature during addition ranged from about 3° C. to about 8° C.

Solvent was removed on a rotary evaporator to yield 165 grams (94% yield) pale yellow oil which solidified on standing.

Gas chromatographic area percent indicated 0.9% chlorobenzene, 95% bis(2,4-dichlorophenyl) chlorophosphate, 1.4% 2,4-dichlorophenyl-2,6-dichlorophenyl chlorophosphate, and 1.2% tris(2,4-dichlorophenyl) phosphate. The true assay of bis(2,4-dichlorophenyl) chlorophosphate was determined by gas chromatography against an internal standard to be 96.2%.

What is claimed is:

1. A process for preparing diaryl phosphites of improved purity which comprises reacting monosubstituted dihalophosphite, wherein the monosubstituent is a radical which forms a monosubstituted dihalophosphite which can be separated from any impurities, with a sufficient amount of a phenol to provide a diaryl phosphite of improved purity.

2. The process as recited in claim 1 wherein said monosubstituent is an alkyl radical.

3. The process as recited in claim 1 wherein said phenol is 2,4-dihalophenol.

4. A process for preparing alkyl diaryl phosphites which comprises reacting an alkyl dihalophosphite wherein the halo radicals can be chlorine or bromine with a phenol to provide an alkyl diaryl phosphite, wherein alkyl is intended to include alkyl, alkenyl, alkynyl, cycloalkyl, cycloalkenyl, cycloalkynyl, heterocyclyl, aralkyl and substituted derivatives thereof; and aryl is intended to include radicals of one or more aryl rings, biphenyl and substituted derivatives thereof.

5. The process of claim 4 wherein alkyl is a $C_1$-$C_4$ alkyl group and halosubstituted derivatives thereof.

6. The process of claim 4 wherein halo is chlorine.

7. The process of claim 4 wherein aryl is the residue of phenol.

8. The process of claim 4 wherein aryl is the residue of 2,4-dihalophenol.

9. The process of claim 4 wherein the compound of alkyl dihalophosphite is used in a purity above 90%.

10. The process of claim 4 which includes the further step of purifying the alkyl dihalophosphite prior to reaction with the phenol.

11. A process for preparing diaryl halophosphates which comprises reacting an alkyl dihalophosphite of the formula $A^1$—O—$PY_2$ with a phenol of the formula $Ar^1OH$ to provide an alkyl diaryl phosphite of the formula $A^1$—O—$P(OAr^1)_2$ and halogenating the alkyl diaryl phosphite to prepare diaryl halophosphates of the formula $(Ar^1O)_2P(O)Y$, wherein $A^1$ represents alkyl, cycloalkyl, heterocyclyl, aralkyl and substituted derivatives thereof; $Ar^1$ represents 1 or more aryl rings, biphenyl and derivatives thereof which are non-reactable with halogen during the halogenation reaction, and Y is chlorine, bromine or iodine.

12. The process of claim 11 wherein $A^1$ is a $C_1$-$C_4$ alkyl group and halosubstituted derivatives thereof.

13. The process of claim 11 wherein Y is chlorine.

14. The process of claim 11 wherein $Ar^1$ is the residue of phenol.

15. The process of claim 11 wherein $Ar^1$ is the residue of 2,4-dihalophenol.

16. The process of claim 11 wherein the compound of alkyl dihalophosphite is used in a purity above 90%.

17. The process of claim 11 which includes the further step of purifying the alkyl dihalophosphite prior to reaction with the phenol.

* * * * *